(12) United States Patent
Liu

(10) Patent No.: US 6,886,139 B2
(45) Date of Patent: Apr. 26, 2005

(54) METHOD AND APPARATUS FOR MANAGING INFANT CARE

(76) Inventor: Yadong Liu, 5904 Rainbow Dr., San Jose, CA (US) 95129

( * ) Notice: Subject to any disclaimer, the term of this patent is extended or adjusted under 35 U.S.C. 154(b) by 522 days.

(21) Appl. No.: 09/969,376

(22) Filed: Oct. 1, 2001

(65) Prior Publication Data

US 2003/0063135 A1 Apr. 3, 2003

(51) Int. Cl.$^7$ .............................................. G06F 17/00
(52) U.S. Cl. ........................ 715/864; 715/963; 368/10; 340/309.4; 607/5
(58) Field of Search ............................. 368/10, 23, 28, 368/82, 223; 340/309.4; 560/185; 607/5, 60; 715/864, 963; 705/2, 3; 345/774, 864, 865, 963, 965, 970

(56) References Cited

U.S. PATENT DOCUMENTS

| | | | |
|---|---|---|---|
| 5,691,932 A | * 11/1997 | Reiner et al. ................. | 368/10 |
| 6,208,897 B1 | * 3/2001 | Jorgenson et al. ............. | 607/5 |
| 6,246,975 B1 | * 6/2001 | Rivonelli et al. ............. | 703/11 |
| 6,735,479 B2 | * 5/2004 | Fabian et al. ................. | 607/60 |
| 2002/0038047 A1 | * 3/2002 | Gelling et al. ............... | 560/185 |
| 2003/0037063 A1 | * 2/2003 | Schwartz ................. | 707/104.1 |

* cited by examiner

Primary Examiner—Ba Huynh
(74) Attorney, Agent, or Firm—Joe Zheng

(57) ABSTRACT

A generic solution is disclosed to facilitate and improve the management of infant care, the complex nutritional and health requirements of infants. According to one embodiment, a portable device collects information regarding the subject infant and can manually or automatically configure various reminders for a caregiver to attend to the infant under care. According to another embodiment, based on the collected information, the apparatus configures reminders in accordance with associated product information (i.e., product nutrition, serial numbers and use information). As a result, a caregiver can be always reminded of what, when and how much of infant products an infant shall be fed with.

28 Claims, 13 Drawing Sheets

Baby Formula selection — 328

1. AAA
> 2. BBB
3. CCC
4. DDD next

---

332

Time to feed

---

320

Enter name: Princess Smith
Birth date: June 1, 2000
weight at birth: 4.2 kilograms
gender: Male
Current date: June 9, 2000
Current time: 10:30:00 AM next — 324

322

---

330

11:20 AM

334

1. Warm up one cup of water to 50 degree;
2. mix 5 grams of the formula with the warmed water; and
3. Add 0.5 grams of X element

Feed Princess with 5 grams of BBB formula

[ how ]

*Fig. 3F*

METHOD AND APPARATUS FOR MANAGING INFANT CARE

BACKGROUND OF THE INVENTION

1. Field of the Invention

The present invention relates to a method and apparatus for managing infant care. More specifically the present invention relates to a method and system for providing reminders to a caregiver as to when, how and what to feed an infant or what to do with the infant.

2. Description of the Related Arts

Before the 20th century infants who couldn't be breast-fed could hardly survive. Today, although breast-feeding is still considered as the best source of nutrition for infants, infant formula has reached to a state where it supplies a considerable portion of the nutrients available in breast milk. Infants properly nurtured with the present baby formulas thrive.

The Infant Formula Act was signed into federal law in 1980 after deficient formula hit the market which possibly caused infant deaths. Realizing that there were no guidelines to oversee formula production, US Congress introduced this law and gave the FDA authority to set the standard for and monitor infant formula production. FDA regulations specify exact nutrient level requirements for infant formulas, based on recommendations by the American Academy of Pediatrics Committee on Nutrition. The following must be included in all formulas: Protein, fat, linoleic acid, vitamin A, vitamin D, vitamin E, vitamin K, thiamine (vitamin B1), riboflavin (vitamin B2), vitamin B, vitamin B12, niacin, folic acid, pantothenic acid, vitamin C, calcium, phosphorous, magnesium, iron, zinc, manganese, copper, iodine, sodium, potassium, and chloride. In addition, formulas not made with cow's milk must include biotin, choline and inositol (U.S. Food and Drug Administration, FDA Consumer, September 1990, Updated: March 1991).

As the popularity of infant formulas and foods has grown so have the complications associated with it. One of the primary considerations a parent must confront is how to feed an infant with a correct amount at an appropriate time. A young mother typically lives away from her experienced own mother and probably the only source to get information about an infant product is to learn from the labeling. However, there have been problems with the manufacturers and labeling of infant foods in the past that have resulted in many recalls. Between 1982 and 1994 there have been 22 "significant" product recalls associated with infant formula, seven of which were classified as Class I, potentially life threatening (Babbitt, "*FDA Recalls Baby Formula,* 1998"). In 1999, 120,000 cans of Mead Johnson's ProSobee formula were recalled for labeling errors after a parent called the company to inquire why the product smelled strange. It was discovered that cans labeled as infant formula contained, in fact, Vanilla Sustacal, an adult nutritional supplement that, if consumed by infants, could lead to what the Mead Johnson Corporation itself calls "severe medical problems" (Mead Johnson press release, Jun. 5, 1999). Evidently, learning or getting experiences from the labeling how to take care of an infant would be a dangerous endeavor.

New parents are generally given limited information regarding the nutrition of their new infant. This information will generally consist of a basic schedule and a starter kit including baby care items and samples of infant formulas. The general schedule generally resembles the following:

There is therefore a great need for an infant care and management system that reminds a caregiver of when, how, what to feed an infant. Further there is a growing need to your mothers for an infant nutrition and health management system that can facilitate and improve the management of the infant's complex nutritional and health requirements.

SUMMARY OF THE INVENTION

In consideration of the above and other needs, a method and an apparatus for managing infant care are disclosed. According to one aspect of the present invention, an electronic device is configured to be portable and/or wearable. The device is loaded with a set of norm data that represents how a "normal" child or a group of children grow. While the device provides reminders to a caregiver, feeding information is collected over the time and a comparison can thus be provided between a child under care with the device and the "normal" child so that the caregiver knows how his/her child grows physically.

According to one embodiment, the device is designed to be presentable like a toy that preferably stays close to a child under care. The device sends a noticeable reminder of what, when and/or how much of infant products the child shall be fed with or what to do with the child. In one application, the reminders are automatically configured with respect to received information about the child. These reminders are typically those that are regular or constantly used, such as reminders for feeding the child, changing diapers or putting the child into sleep. In another application, the reminders are manually entered. These reminders are typically used to remind the caregiver of what to do with the child, examples including having the child taken a medication at a specific time shall the child be sick.

According to another aspect of the present invention, a system and method, referred to herein alternatively as an Intelligent Infant Care (IIC) system, is configured to facilitate and improve the management of the complex nutritional and health requirements of infants. The system collects information regarding the subject infant (i.e., birth date and time, birth weight, periodic weights, medical issues such as allergies and other medical conditions of note, physician recommendations, diaper changes etc.). Based on the collected information, the system configures reminders in accordance with associated product information (i.e., product nutrition, serial numbers and use information). As a result, a caregiver can be always reminded of what, when and how much of infant products an infant shall be fed with.

According to yet one aspect of the present invention, an apparatus for managing infant care is disclosed. The apparatus may be, but not be limited to, a portable device, a palm computing device, a cellular phone or a computer and is loaded with an application that receives infant data and configures reminders in accordance with product information of one or more selected products to be supplied to an infant. The reminders are then sequentially activated over time to remind a caregiver of what, when and how much of an infant product the infant shall be fed with. Each of the reminders may be configured to supply detailed instruction how the infant product shall be used.

Typically, the apparatus includes a user interface including a display screen and an input mechanism, a memory device for storing infant data entered through the input mechanism, a client module, when activated by a processor, computing the reminders according to at least an infant product with respect to the entered infant data, each of the reminders to be activated sequentially by the client module when an appropriate time comes, and each of the reminders causes a message to be displayed on the display screen.

According to still another aspect of the present invention, the system or apparatus can access third party information resources (i.e., FDA and manufacturer registration information) that include up to date infant nutritional standards and related health related advisories. Infant specific information (i.e., product identification information and use information) is compared to the registered information and infant requirements and a determination is made as to the appropriate feeding instructions based on previous entries (i.e., feeding history), product nutritional information and authoritative guidelines (i.e., FDA guidelines).

Additionally, the system provides resources for generating warnings when nutritional intake does not meet predefined nutritional standards (i.e., a nutritional parameter not meeting the minimum standard in a defined period of time). These warnings may take the form of a visual indicator on a terminal device display, an audible sound or a message forwarded to a designated remote terminal device.

The foregoing and other objects, features and advantages of the invention will become more apparent from the following detailed description of a preferred embodiment, which proceeds with reference to the accompanying drawings.

BRIEF DESCRIPTION OF THE DRAWINGS

These and other features, aspects, and advantages of the present invention will become better understood with regard to the following description, appended claims, and accompanying drawings where:

FIGS. 3B through 3G illustrate exemplary displays on a display screen of the terminal device in FIG. 3A to show some of the features contemplated by the present invention;

DETAILED DESCRIPTION OF THE INVENTION

Figure 1A:
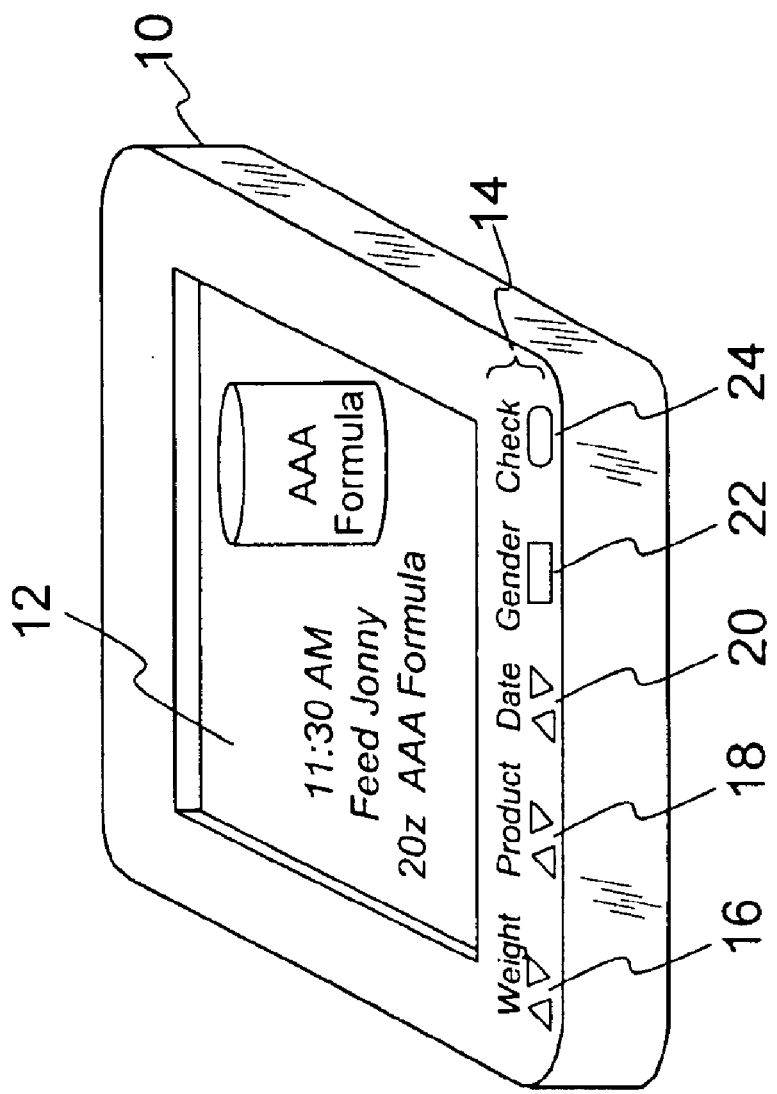
FIG. 1A shows a perspective view of a portable device used to provide reminders to a user thereof according to one embodiment of the present invention.

The invention pertains to a method and a system for managing infant care through a portable device. In one embodiment, the portable device is a dedicated apparatus that receives data entered by a user and provides necessary timed reminders to the user. The portable device may be configured to possess a toy appearance or characteristics so that it may be placed in an infant room or near the infant. The portable device may also be, but not limited to, a cellular phone, a portable or mobile computing device, a palm data assistant. Various types of reminders may be configured in the portable device. Examples of the types include reminders for changing diapers, reminders for feeding a child, reminders for putting a child into sleep and reminders for having a child take a medication shall the child be sick. Optionally, the portable device may include a memory space storing data representing a healthy or normal child or children growth. The data, also referred to as norm data, can be used to compare how the infant under care is physically growing. As a result, the portable device may be used to inform a caregiver of a precaution if an unusual healthy condition starts. According to another embodiment, the portable device is coupled to a data network and accesses one or more servers on a data network to download trusted information resources relating to infant products and/or guidance from regulatory agencies. Unless specifically stated, as used herein, infant product or simply product means various formulas for infants and foods for small children.

According to one aspect of the present invention, a system, sometimes referred to herein as Intelligent Infant Care (IIC) system, provides assistance to a user (e.g. a young mother) in regards to the management of the dietary and health needs of his/her infant. The system collects infant specific health information, consumption information, product identification information and other associated data; analyzes the information, and makes feeding related recommendations (i.e., schedules, amounts etc.) based on manufacturers product information and/or information derived from regulatory agencies (i.e., Food and Drug Administration). More specifically, the present invention utilizes intelligent agents, network based software application modules, data resources from trusted third parties and information other caregivers (i.e., the infant's pediatrician) to deliver timely information related to the scheduling and management of an infant's nutritional and health requirements.

Definitions

Some of the commonly used terms are provided herein to facilitate the description of the invention and should not be interpreted as limitations to the current invention:

Infant data: any data related to an infant or a child under care with the portable device contemplated in the present invention. This may include, but not be limited to, birthday, gender, special care information, consumption information, medical/health information/condition and demographic information in both objective and subjective forms.

Product module: a product may be configured or implemented in a modular fashion, each module is focused on a specific function relating to nutritional and non-nutritional issues. In a preferred embodiment, a product module is a software application or module that may be contained within a single centralized server device or distributed among a plurality of server devices acting as a logical unit.

Knowledge base: an information database comprising static and dynamic information from multiple sources, databases, online or offline resources that may include exact nutrition and/or ingredients of all infant products in the market, recommended approved feeding instructions, governmental regulatory information on the products. The information may be made available to the public by respective manufacturers of various products via the Internet. These databases may be relational or object-oriented databases.

Recorded Infant Data: This generally takes the form of a database (object-oriented and/or relational). This includes all pertinent information related to a particular infant, including received infant data, nutritional and non-nutritional information about the infant.

Terminal or portable devices include but may not limited to personal computers, dedicated electronic devices, laptop computers, computer terminals, network appliances, personal digital assistants, palm-sized computing devices, and networked wireless communications devices such as microbrowser enabled mobile telephones. Such devices typically have a user interface including a display screen, an input interface (i.e. a keypad) and perhaps a pointing device (e.g., a mouse, a trackball, a joystick, a navigational key-set or a touch-pad).

Notation and Nomenclature

In the following detailed description of the present invention, numerous specific details are set forth in order to provide a thorough understanding of the present invention. However, it will become apparent to those skilled in the art that the present invention may be practiced without these specific details. In other instances, well known methods, procedures, components, and circuitry have not been described in detail to avoid unnecessarily obscuring aspects of the present invention.

The detailed description of the present invention in the following are presented largely in terms of procedures, steps, logic blocks, processing, and other symbolic representations that resemble data processing devices coupled to networks. These process descriptions and representations are the means used by those experienced or skilled in the art to most effectively convey the substance of their work to others skilled in the art.

The present invention is related to a method, an apparatus and a system, which facilitates the management of nutritional and health issues related to the care of an infant. The method along with the apparatus and system to be described in detail below is a sequence of processes or steps leading to a desired result. These operations or processes are those requiring physical manipulations of physical quantities. Usually, though not necessarily, these quantities may take the form of electrical signals capable of being stored, transferred, combined, compared, displayed and otherwise manipulated in a computer system or electronic computing devices. It proves convenient at times, principally for reasons of common usage, to refer to these signals as bits, values, elements, symbols, operations, messages, terms, numbers, or the like. It should be borne in mind that all of these similar terms are to be associated with the appropriate physical quantities and are merely convenient labels applied to these quantities. Unless specifically stated otherwise as apparent from the following description, it is appreciated that throughout the present invention, discussions utilizing terms such as "processing" or "computing" or "verifying" or "displaying" or the like, refer to the actions and processes of a computing device that manipulates and transforms data represented as physical quantities within the terminal device's registers and memories into other data similarly represented as physical quantities within the computing device or other electronic devices.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments.

The Preferred Embodiments

Referring now to the drawings, in which like numerals refer to like parts throughout the several views. Referring now to the drawings, in which like numerals refer to like parts throughout the several views. FIG. 1A shows a perspective view of a portable device 10 according to one embodiment of the present invention. The device 10 includes a screen 12 and a set of buttons 14. The screen 12 may be a color or black-and-white LCD screen showing a reminder to a user thereof what to do with an infant monitored by the device 10. Depending on an exact implementation, the set of buttons 14 may include various keys for the user to enter infant data about the infant, check previous or next reminders, select one or more products to use. For example, the device 10 includes a number of up-down buttons 16, 18 and 20 and push buttons 22 and 24. The buttons 16 allow the user to enter the weight of the infant, the buttons 18 facilitates the user to select a particular product to feed the infant, and the buttons 20 asks the user to enter the right birth date of the infant so that the proper reminders could be determined in conjunction with other information about the infant. The button 22 allows the user to tune the device to one gender (baby girl or boy) so that a proper amount of infant food could be determined. The button 24 is provided for the user to check any previous or next reminders. As will be further appreciated below, one of the features in the present invention is to assist young or inexperienced caregiver though the device 10 to take good care of his/her infant. As there are various infant brands or kinds, each may have different nutrition, the amount thereof to be fed to an infant could be different. As another one of the features in the present invention, the device 10 allows the caregiver to select a particular product (via the buttons 18) so that a correct amount of infant food can be determined in conjunction with the entered infant data. For example, the caregiver has been using AAA formula for sometime and now switches to BBB formula. By choosing the currently used formula, an application (e.g. a software or client module) or simply an electronic circuit module in the device 10 will automatically re-determine the reminders so that the infant always receives the correct amount of nutrition to grow properly.

The reminders determined by the application resident in the device 10 is time based. In other words, each of the reminders will go off sequentially when an appropriate time comes. In one embodiment, a reminder is set to go off at 11:30 AM and activated when the time is 11:30 AM. As shown in the figure, the reminder includes information about who shall be attended to and how much of a type of formula should be given. Alternatively, a detailed instruction may be provided and displayed if the user actives a dedicated button. It should be noted that the information contained in each of the reminders may not be the same and typically varies as the infant grows and/or the infant product in use changes.

According to one embodiment, the device 10 is configured to provide a number of types of reminders that may include, but not be limited to, feeding times, diaper change times, sleeping times, and medication times. Some of the types of the reminders can be automatically configured and periodically timed and others may be manually set for a limited duration. For example, based on the infant information (e.g. gender, age and weight), the feeding times or the diaper changes can be automatically determined. Should the child be sick, the medication times can be manually configured as well according to instructions provided by a doctor.

Figure 1B:
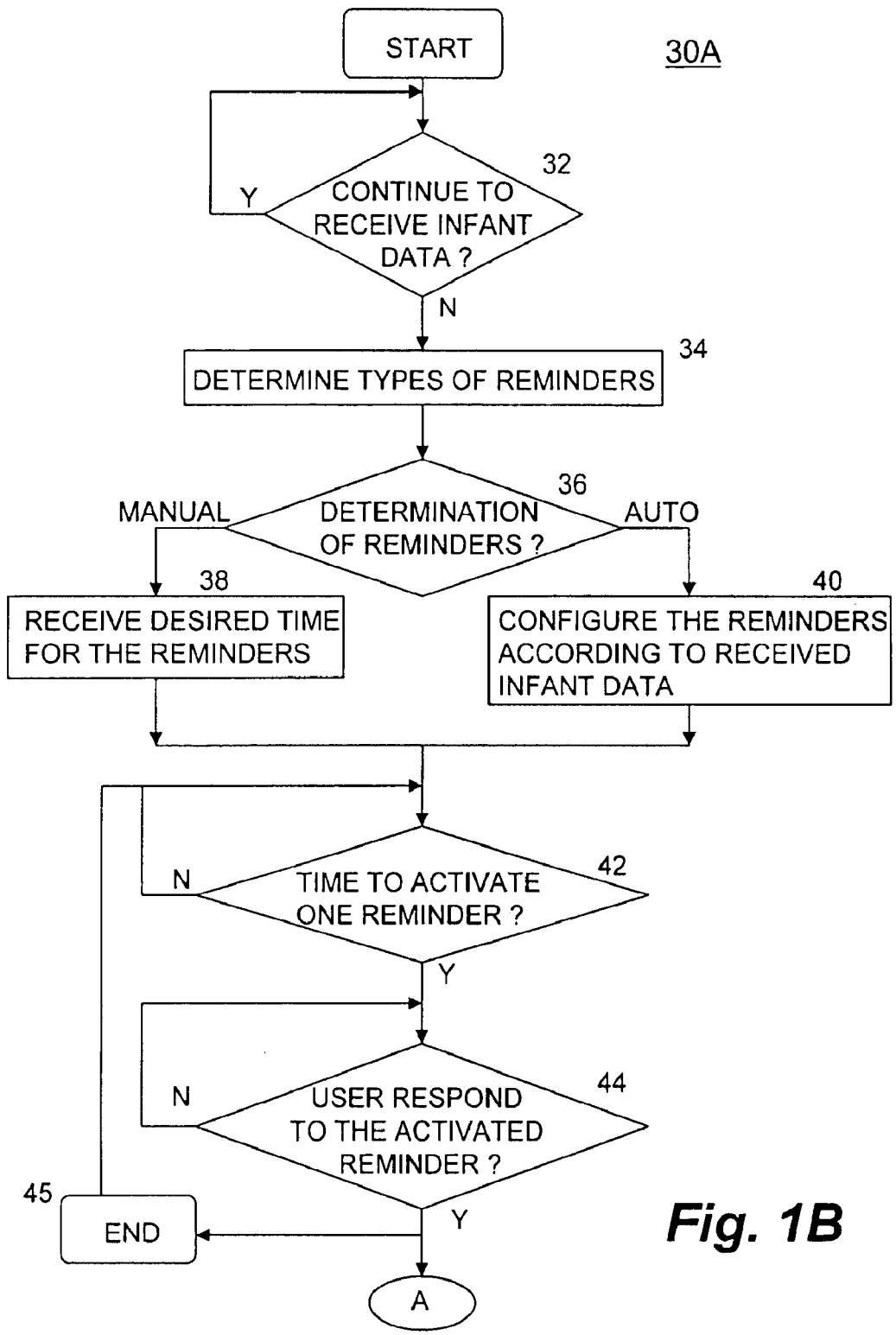
FIGS. 1B and 1C show an exemplary process flowchart of operations in a portable device contemplated in the present invention.
Figure 1C:
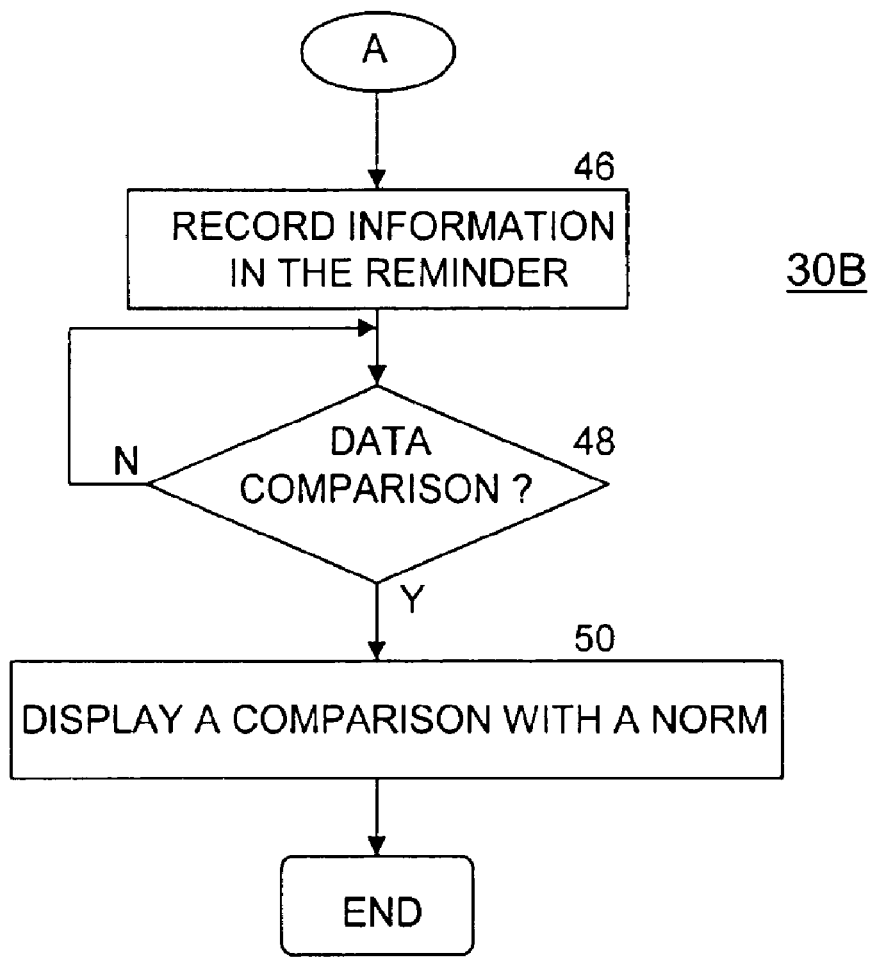

FIGS. 1B and 1C show an exemplary process flowchart 30A and 30B of operations in a portable device contemplated in the present invention. At 32, the portable device requests information about a child under care. The information may include, but not be limited to, name, gender, current age and weight, In some case, the information requested may also include birth date and birth weight of the child. Depending on an exact implement of the device, the requested information may be sequentially inputted from one or more buttons on the device. In a more advanced implementation, the information may be entered from a computer that then transmits the information to the device by a wire or wireless means (e.g. a USB cable or infrared).

After the requested information is received, the device allows the user to determine what type of reminders is needed. This is largely dependent on the use of the device. In a first case, the user needs only one type of reminders, e.g. to be reminded of when the child under care shall be fed. In a second case, the user needs more than one types of reminders. Each of the reminders may be activated in different audio sounds or displays. For instance, a first type of reminders is for reminding the user of the time the child under care shall be fed, a second type of reminders is for reminding the user of the time of changing the diaper for the child, and a third type of reminders is for reminding the user of the time the child shall go to sleep. In any case, the user has an option of how to set the reminders at 36, which is, however, subject to the type of reminders in reality. When the reminders are used for only reminding the user of the time to feed the child or something special to the child, the reminders can be determined manually at 38. In one embodiment, the reminders are set up more or less like making appointments in a calendar. The user needs to select the times or duration for the reminders. For example, a reminder can be manually set at 10:00 AM to feed the child 8 oz of liquid formula and subsequent reminders can be set manually at 2:00 PM, 6:00 PM, and 10:00 PM. The manual determination of the reminders is useful for certain applications besides to reminding the time of feeding a child. For example, should the child be sick and a medication be prescribed therefor, the user can manually set up a sequence of reminders just for the time the child shall take the medication.

According to one embodiment, a certain type of reminders can be automatically configured at 40. The type of reminders is typically for a periodic use, for example, for feeding the child, for changing diapers and for putting the child into sleep. The automatic configuration of the reminders is typically based on a set of norm data and with respect to the received data at 32. For example, a set of norm data, collected from a group of children or recommended/provided by an organization, a governmental agency, a nutritionist and/or pediatrician, suggests a feed frequency based on the gender, current age, current weight of the child. The frequency determines the reminders, for example, every 3 hours to feed 6 oz of formula at 4 months old. The frequency shall gradually change as the child grows. A further detailed description of automatically configuring the reminders with respect to the received information about the child is provided below.

Once configured either manually or automatically, the reminders are set to go. Typically the reminders are activated by an internal clock at 42. For example, a feeding reminder is set off at 10:10 AM, when the time comes, the reminder goes off by alerting a caregiver. The alerting means includes producing an audio sound (e.g. an alarm or a music) and/or displaying a specially designed display (e.g. a fleshing an image or message). At 44, the process 30A awaits a response from the caregiver. In response to the reminder, the caregiver may push/activate a designated button on the device. In one implementation, the process 30A ends by going to 42 to wait for another reminder to go off when an appropriate time comes. In another implementation (e.g. an advanced version of the portable device), the process 30A goes on to 30B in FIG. 1C.

Figure 1D:
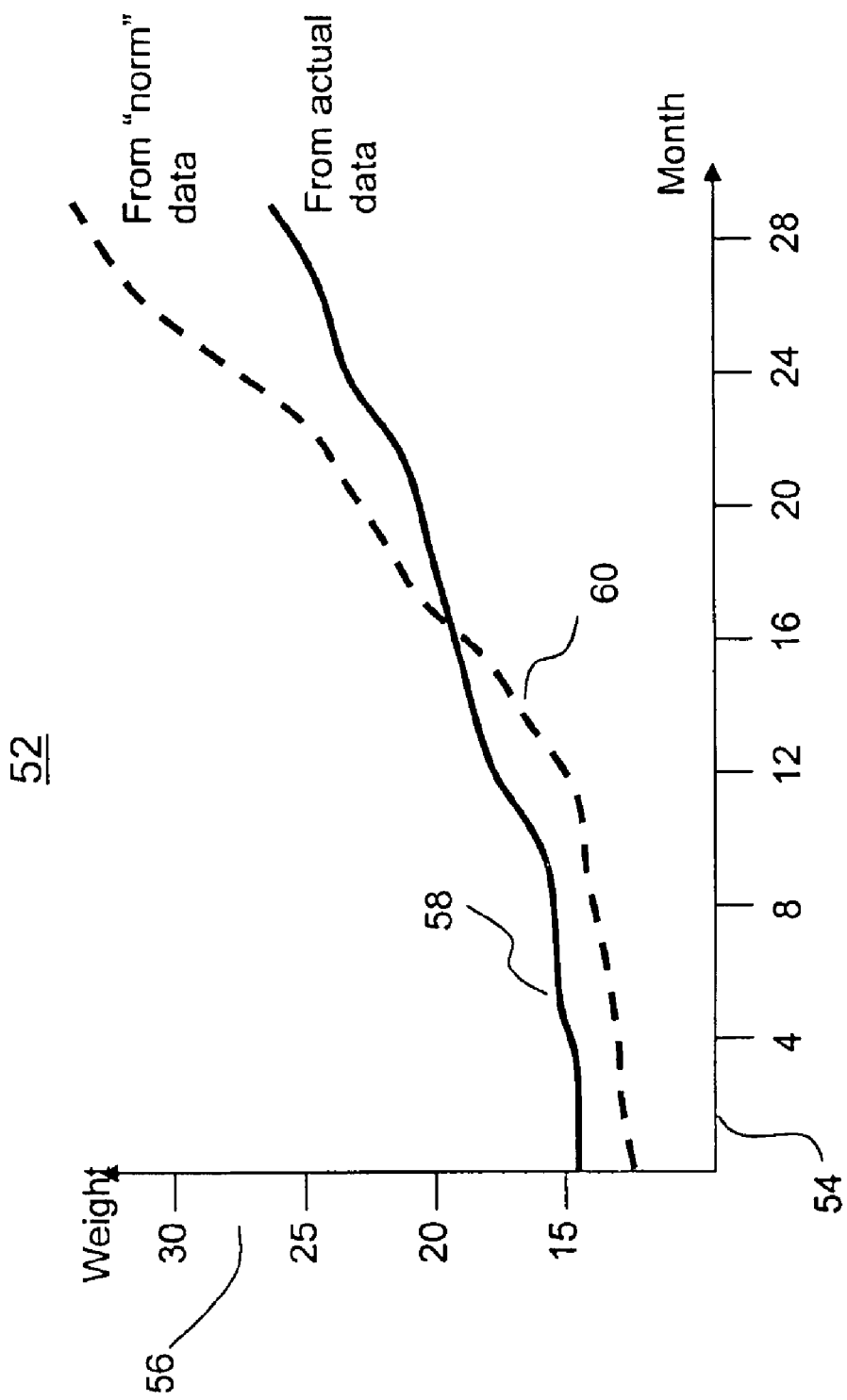
FIG. 1D shows an exemplary chart that may be displayed on a screen of the device of FIG. 1A and indicates a graphic comparison between two curves derived respectively from two sets of data.

Once the caregiver responds to a reminder, the information in the reminder is noted or recorded in a module in the device. For example, if a reminder is to remind a caregiver to feed a child a certain amount of formula at a specific time, the feeding information is collected based on the assumption that the caregiver follows the reminder. Alternatively, the caregiver can enter exactly how much formula has been given to the child. If needed by the caregiver, a comparison of the child with a "normal" child can be performed at 48. The "normal" child or a group of children is based on a set of norm data representing a child growth in a normal situation. In one example, the norm data shows how a "normal" child shall be at a particular age so that the caregiver can get an idea how the child under his/her care develops in comparison with the "normal" child. Upon activating a designated button in the device, a comparison in text, table or graph is displayed at 50. FIG. 1D shows an exemplary chart 52 that may be displayed on a screen of the device and indicates a graphic comparison between two curves 58 and 60 derived respectively from two sets of data. In particular, the horizontal and vertical axes 54 and 56 represent age growth and corresponding weights. The curve 60 is derived from a set of "norm" data and the curve 58 is derived from the data collected over time from the reminders, with periodical inputs from the caregiver.

It should be noted that the chart 52 is an example. Other graphic representation (i.e. height) may be possible depending on an specific implementation and need. One of the benefits in the present invention is to provide a brief comparison to the caregiver how the child under his/her care develops in view of other children. If the comparison indicates something extraordinary, a precaution or pediatric advice may be sought timely.

Figure 1E:
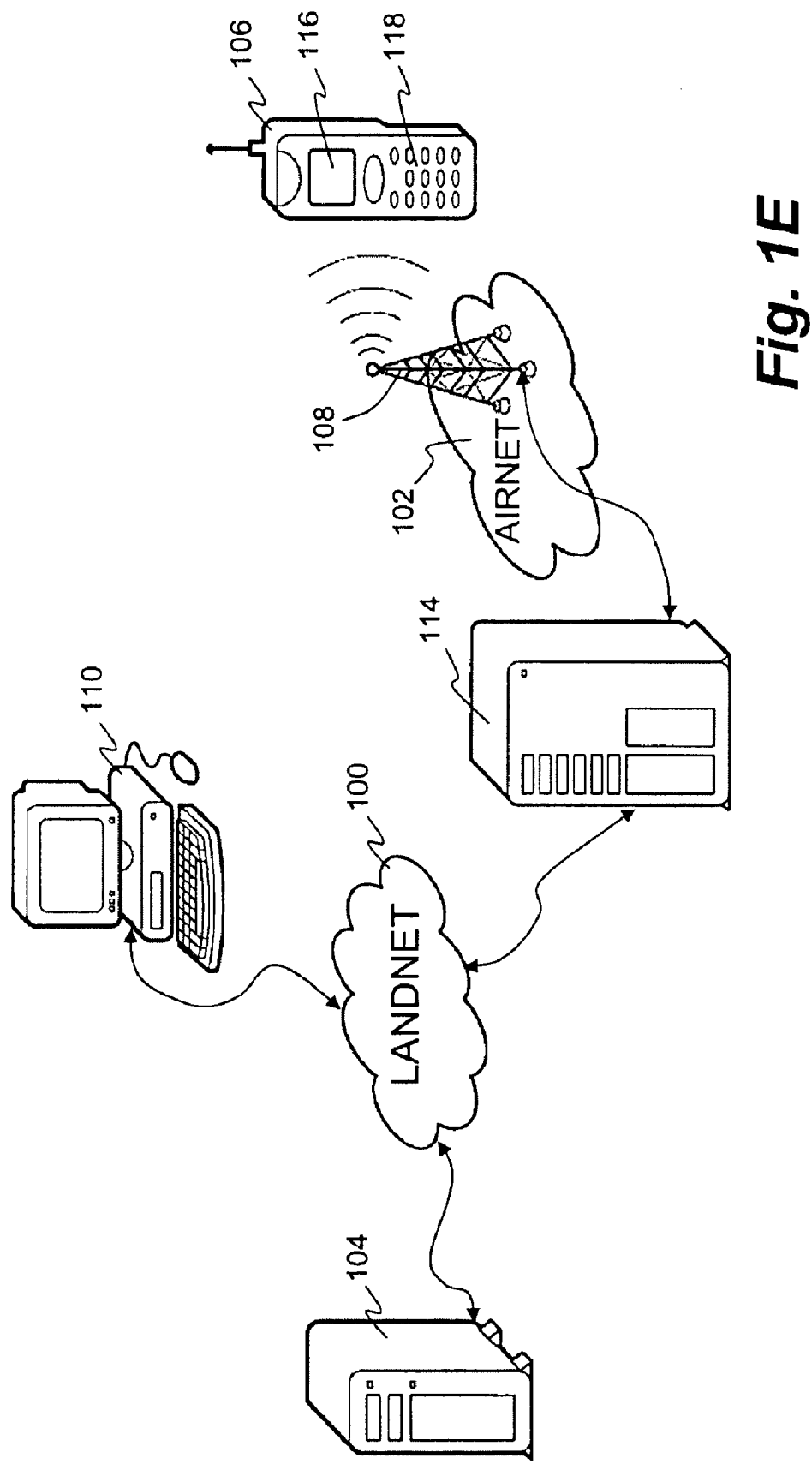
FIG. 1E is a block diagram of a communications system which may be used to implement a method and system embodying the invention.

The current information technology infrastructure has penetrated into every aspect of life. Many people carry one or two computing devices, such as a Palm Pilot or a data-enabled mobile phone. One of the features in the present invention is to utilize these portable computing devices to achieve the functions or results that would otherwise be achieved in a dedicated electronic device. FIG. 1E illustrates a schematic configuration in which the present invention may be practiced in accordance with another embodiment utilizing the information technology infrastructure available today. Landnet 100 is a landline network that may be the Internet, the Intranet and a data network of other private networks. Coupled to landnet 100 are a personal computer (PC) 108 and a network server 104. Personal computer 108 may be a desktop computer from which various product modules may be loaded to network server 104. According to one embodiment, network server 104 is operated by a manufacturer providing a series of products for infants to toddlers and hosts knowledge database and/or product modules for the respective products. In one example, a product module includes specific information about an infant formula along with feeding instructions as to when and how much an infant of a certain age shall be fed with the formula. The information stored in network server 104 may be in form of text or hypermedia and accessible through a common communication protocol.

Serviced by airnet 102 is a terminal device, though a representative of a cellular phone 106 is shown in the figure. Terminal device 106 is capable of communicating, via airnet 102, wirelessly with antenna 108. For simplicity, antenna 108 also represents a wireless carrier infrastructure that generally comprises a base station and an operations and maintenance center. The base station controls radio or telecommunication links with the mobile devices. The operations and maintenance center comprises a mobile switching center performing the switching of calls between the mobile devices and other fixed or mobile network users. Further the operations and maintenance center manages mobile services, such as authentication and oversees the proper operation and setup of the wireless network. Each of the hardware components and processes in carrier infrastructure 108 are known to those skilled in the art and not to be described herein to avoid unnecessarily obscuring aspects of the present invention.

Between landnet 100 and airnet 102 there is a server device 114 functioning as a proxy server which, also referred to as link server or network gateway server. Proxy server 114 couples airnet 102 to landnet 100 to facilitate the communication between server device 104 and terminal device 106 if necessary.

Figure 2A:
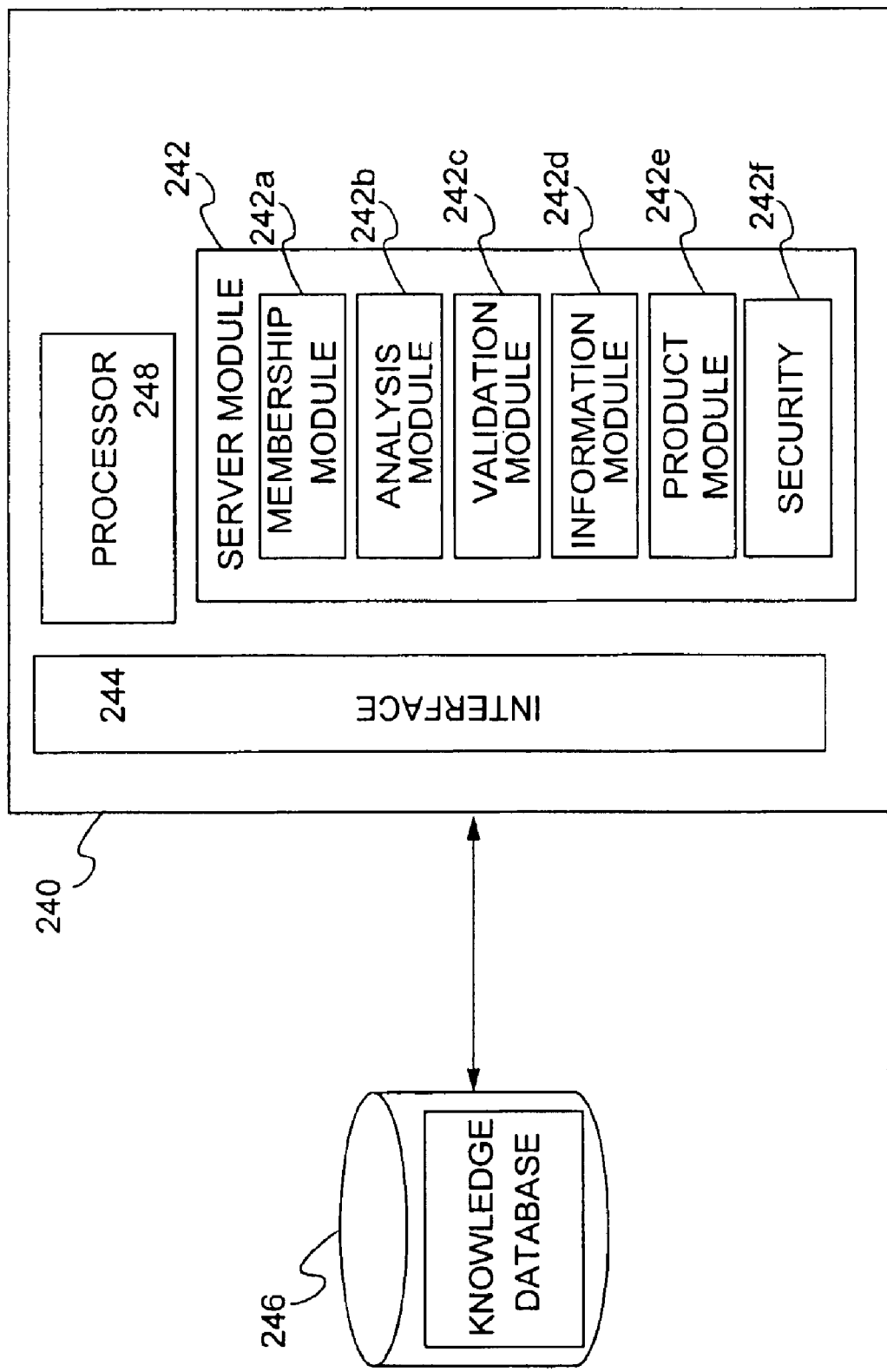
FIG. 2A illustrates a representative server device that may correspond to a server device used in FIG. 1.

FIG. 2A illustrates a representative server device 240, which may correspond to server device 104 of FIG. 1. In accordance with an embodiment of the present invention, server 240 may be operated by a business entity in food industry or an agency administrating infant nutrition or health. Typically server device 240 includes a processor (or multi-processor), a server module 242 and a database 246. In practice, any computing device having reasonable computing resources (i.e., processing power and memory capacity) may be utilized as server device 240.

According to one embodiment of the present invention, server module 242 is a compiled and linked version of a computer language implementing the present embodiment and loaded in a memory. When executed by server 240, server module 242 performs a number of functions to facilitate the operations associated with a preferred embodiment of the present invention.

Server module 242 comprises a membership module 242a, nutritional analysis engine 242b, product validation module 242c, information exchange module 242d, product module 242e and security module 242f. Membership module 242a provides account initialization, management and service functions for a plurality of user accounts associated with users having access to the server. In one embodiment, membership module 242a is a collection of personal accounts, each for a child. Typically, a user or custodian of a child is permitted to update data records in the child account from a terminal device. For example, if the child is sick, the corresponding account can be updated to reflect the particular health condition of the child so that the infant data that determines when and how much formula shall be given to the child shall be adjusted accordingly.

Nutritional analysis engine 242b provides recommendations related to the management of an infant's nutritional care based on provided information from the caregiver, previous consumption entries, product information and guidance from regulatory agencies (i.e., FDA) and perhaps, inputs from participating third parties (i.e., the infant's pediatrician).

Product validation module 242c facilitates information exchange between server 240 and a trusted third party providing information relating to the nutritional parameters of a product of interest (i.e., baby formula). According to one embodiment, the information provided by the third party may include nutritional information of a similar product so that a comparison may be made to ensure that the product of interest is not off line to cause any unexpected results from a child who intakes the product of interest.

Information exchange module 242d may coordinate with any possible governmental agencies that monitor any specific product being offered. In a case that a new guideline promulgated by the government with respect to a particular product or products in similar category is received, necessary or timely precautions may be taken to prevent products in concern from being further used. Security 242f administrates secure links between a terminal device and server 240.

FIG. 2A is provided as an exemplary implementation of a network server by a manufacturer to provide infant care services to users. It is understood to those skilled that the exemplary functional blocks in server 240 would make the present invention more efficient, however, not each of the blocks must be implemented in order to practice the invention.

Figure 2B:
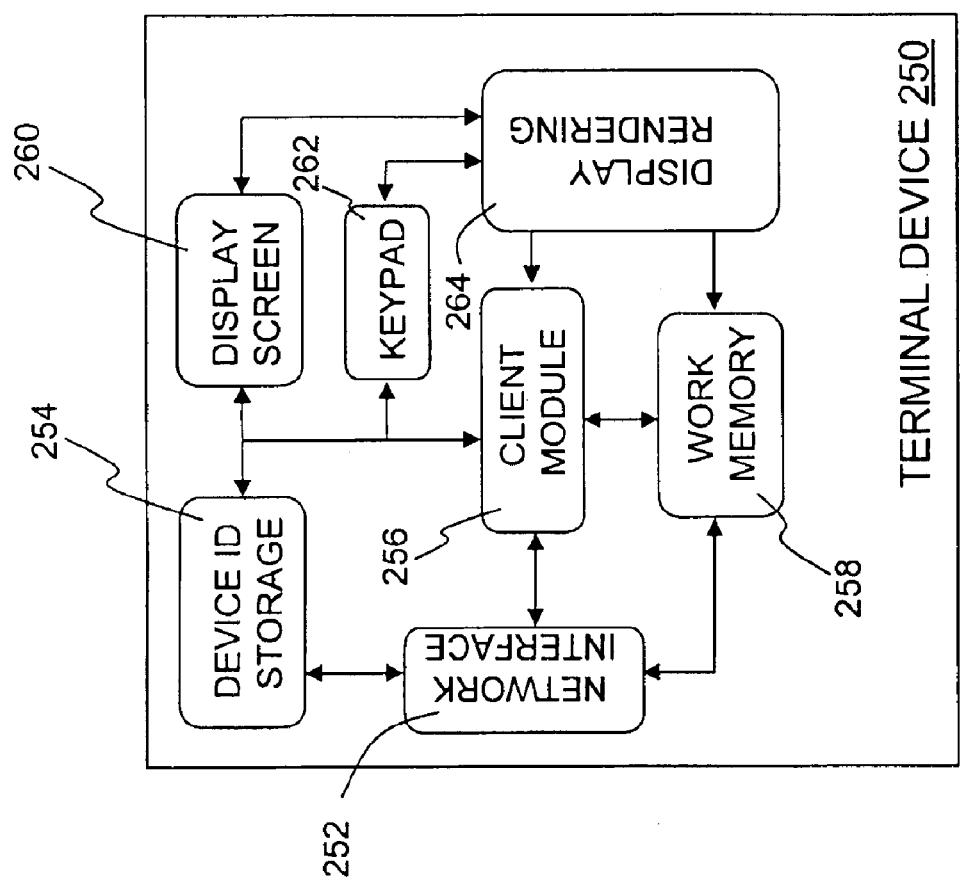
FIG. 2B illustrates a representative terminal device that may correspond to a device used in FIG. 1.

FIG. 2B illustrates a representative terminal device 250, which may correspond to device 106 of FIG. 1. Depending on an exact implementation, terminal device 250 may be a dedicated infant care device, a mobile phone, a desk computer or a portable computing device. According to one embodiment, terminal device 250 includes a client module 256, working memory 258 and a user interface including a display screen 260 and a keypad 262. The client module is a linked and complied version of a computer language implementing the present invention and, when executed by a processor therein, performs functions desired in the present invention as will be further described below.

According to one embodiment, client module 256 is activated to provide reminders to a user who is taking care of an infant. Working memory 258 hosts product information, for example, a specific baby formula and recommended usage. After the user enters the infant data (e.g. birth date, weight, height, gender) into the terminal device from the keypad 262, client module 256 computes the reminders according to the infant data and the product information and the recommended usage. When a time comes, a reminder is activated by client module 256 and displayed on the display screen showing the use of the product. Specifically, display screen 260 shows that an appropriate amount of the product shall be used. In an alternative embodiment, more screens may show details of the use of the product. For example, "mix 10 grams of the formula with one cup of water of 50 degree".

According to another embodiment, terminal device 250 further includes device identifier storage 254 and a network interface 252. Terminal device 250 is assigned a device ID that is stored in device identification storage 254. Device ID can be a phone number of the device or a combination of an IP address and a port number, for example: 204.163.165.132:01905 where 204.163.165.132 is the IP address and 01905 is the port number. The device ID may be further associated with a user ID authorized by or singed up with a wireless carrier or a product manufacturer as part of the procedure to activate a user account for terminal device 250.

Network interface 252 facilitates data communication with a network server (e.g. server 240 in FIG. 2A) via a RF transceiver (not shown in the figure) to receive incoming and outgoing data signals. Device identifier (ID) storage 254 supplies a device ID to network interface 252 so that all messages transported over the network can be identified and properly received. In addition, client device 250 includes a display rendering module 256 that performs display process of received data from the network. In one embodiment, the display rendering module 256 is a micro-browser that, in conjunction with client module 256, performs communication session with a server device via a network 208, requesting and receiving data from the network, display information on display screen 260 thereof, and receive user input from keypad 262 as well.

Figure 3A:
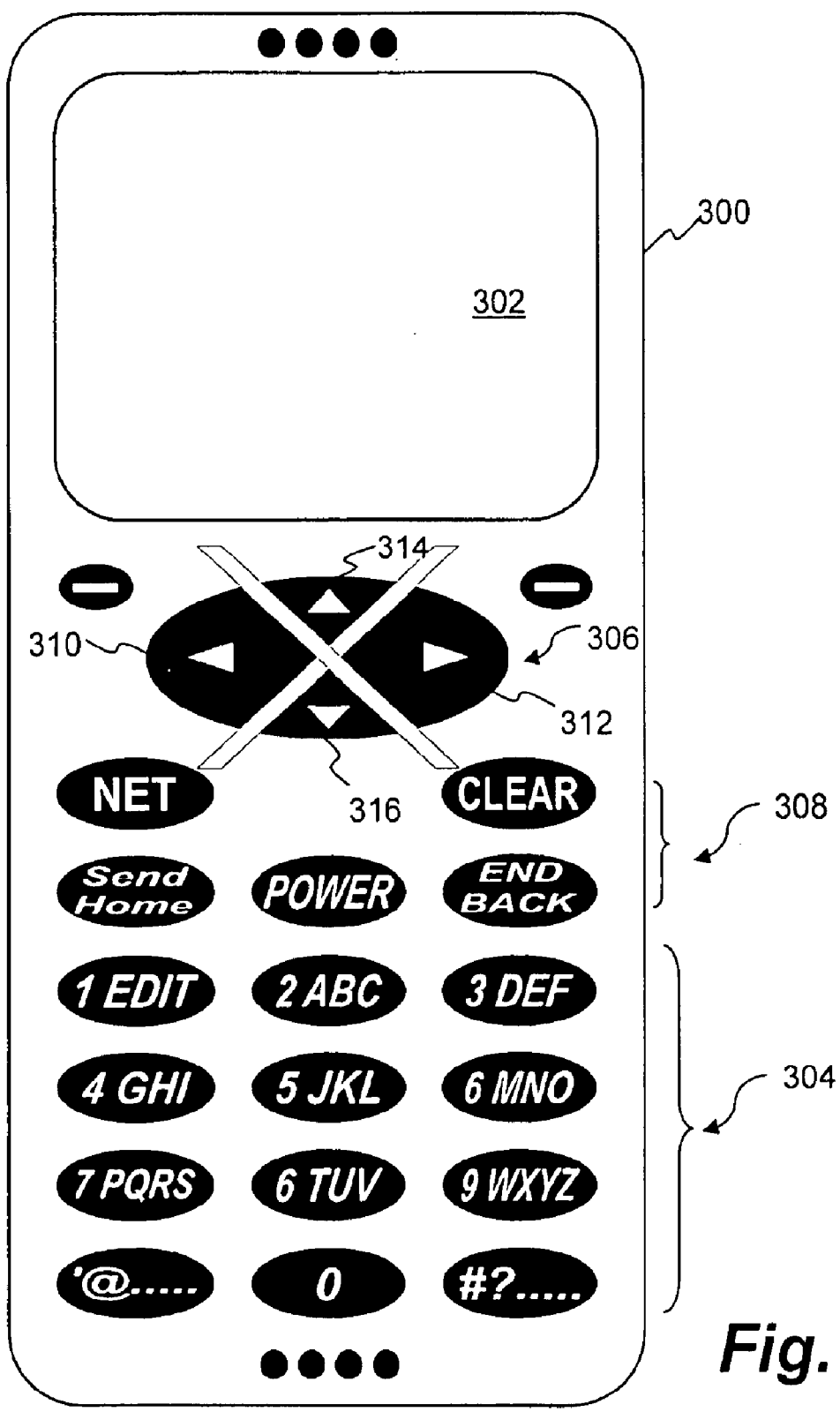
FIG. 3A shows an exemplary terminal device in which the present invention may be practiced to remind a user of timely care giving to an infant.

Prior to describing the invention in further detail, several illustrative examples of applications that can be implemented according to the principles of this invention are described. These applications are illustrative only and are not intended to limit the invention to the particular applications and features described. Referring now to FIG. 3A, there is shown an exemplary terminal device 300 in which the present invention may be practiced to remind a user of timely care giving to an infant. Terminal device 300 includes a screen 302 (e.g. a LCD screen), a set of navigational keys 306 and a phone-like key pad 304 and additional functional keys 308. In one use, screen 302 is used to display detailed information when a reminder is activated so that a user thereof will understand what to proceed next. Navigational keys 306 permits to navigate displayed information. Sometimes, the displayed information may include one or more hyperlinks that like to even more detailed information about a product or a procedure. The phone-like key pad 304 allows the user to enter texts and interact with the terminal device. It should be noted that a miniature-sized keyboard may be used. Alternatively screen 302 may be a touch screen to allow the user to enter data in lieu of the key pad 304. In any case, terminal device 300 includes an input mechanism for the user to enter data necessary to receive personalized reminders.

Figures 3B, 3C, 3D, 3E:

FIGS. 3B through 3G illustrate representative displays. Referring to FIG. 3B, there is shown a typical introductory content page 320. Content page 320 requests infant data necessary to make the client module personalized. Through the user interface (e.g. the screen and the keypad), a caregiver enters the infant data as shown in bold in response to the pertinent questions, for example, the name of the subject infant, his birth date, weight at birth, gender, the current date and time. Depending on the exact implementation, other related information about the infant may be provided as well, such as health related questions. Upon finishing entering the infant data, the user may proceed to the next display by activating an icon or soft key "next".

FIG. 3C illustrates an exemplary screen showing a menu of related products from which the user decides what to use for the infant. In some case, the terminal device may include information on more than one similar infant products, such as AAA formula, BBB formula, CCC formula and DDD formula, each having its own flavor or nutrition levels. Using the navigational keys 306, the user can choose a desired product or brand. Alternatively, a display may be provided to support the selection by showing the detailed ingredients or nutrition information. For example, Vitamin A: 350 IU, Vitamin B6: 45 MCG, and etc. for a selected brand. After a selection is made, the terminal device is now in a waiting mode as shown in FIG. 3D showing a clock. According to one embodiment, a clock is displayed. In another embodiment, one or more related product advertisements may be displayed in a rolling fashion in the waiting mode.

FIG. 3E illustrates an exemplary waking-up mode that is started by a reminder determined by the client module.

When it is time for a predetermined reminder to activate, the client module automatically loads a waking-up sign or icon so that the user is notified that a reminder is waked up. Alternatively, a beeper and a ringing sound is made off to alarm the user that a reminder needs attended. According to one embodiment, when the user is notified of the reminder, the user may interact with the screen to see what needs to be attended. FIG. 3F shows an exemplary screen 334 including a soft key that can be activated to proceed to a next screen 334 in FIG. 3G in which a detailed instruction is provided. As one may appreciate, one of the features in the present invention is to help those inexperienced caregiver provide proven care to his/her infant. Another of the features in the present invention is that the reminders are configured according to a selected product.

Figure 4:
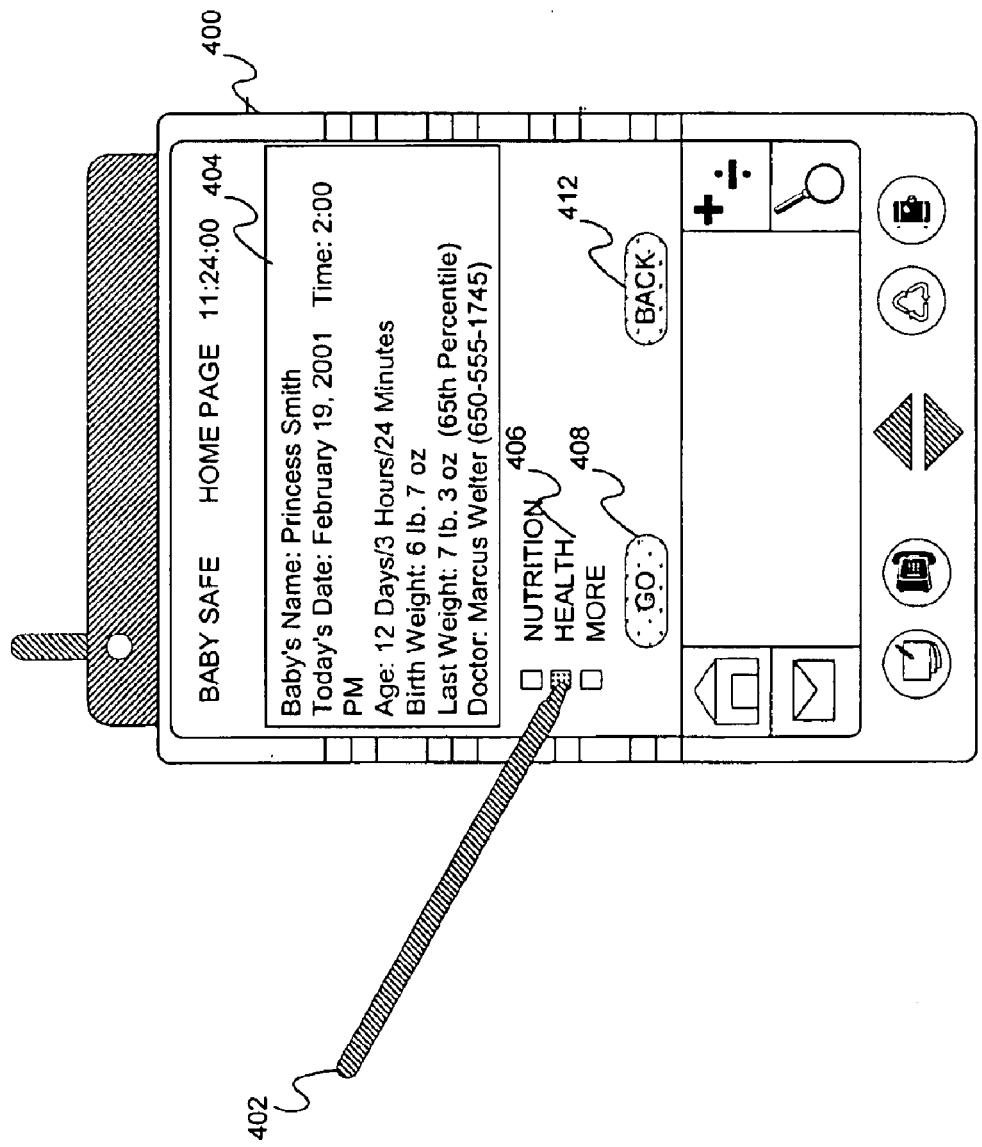
FIG. 4 illustrates a wireless terminal device (a PDA) displaying a graphical user interface screen suitable for interacting with a server operated by a business providing infant products or administrating product information of the infant products.

FIG. 4 illustrates a wireless terminal device (a PDA) displaying a graphical user interface screen suitable for practicing the present invention. According to one embodiment, the application for configuring reminders and timely activating the reminders may be downloaded into the device as such the PDA serves as a baby caring device contemplated in the present invention. In addition, the PDA may be equipped with wireless communication capability so that product information or baby data can be transported between the device and a related server on the network. The illustrated page PDA 400 is comparable to the content found in FIG. 3B. Similar pages could be generated for other devices (i.e., personal computers and network cellular phones) and in markup language format (e.g. HTML or WML)

Figure 5:
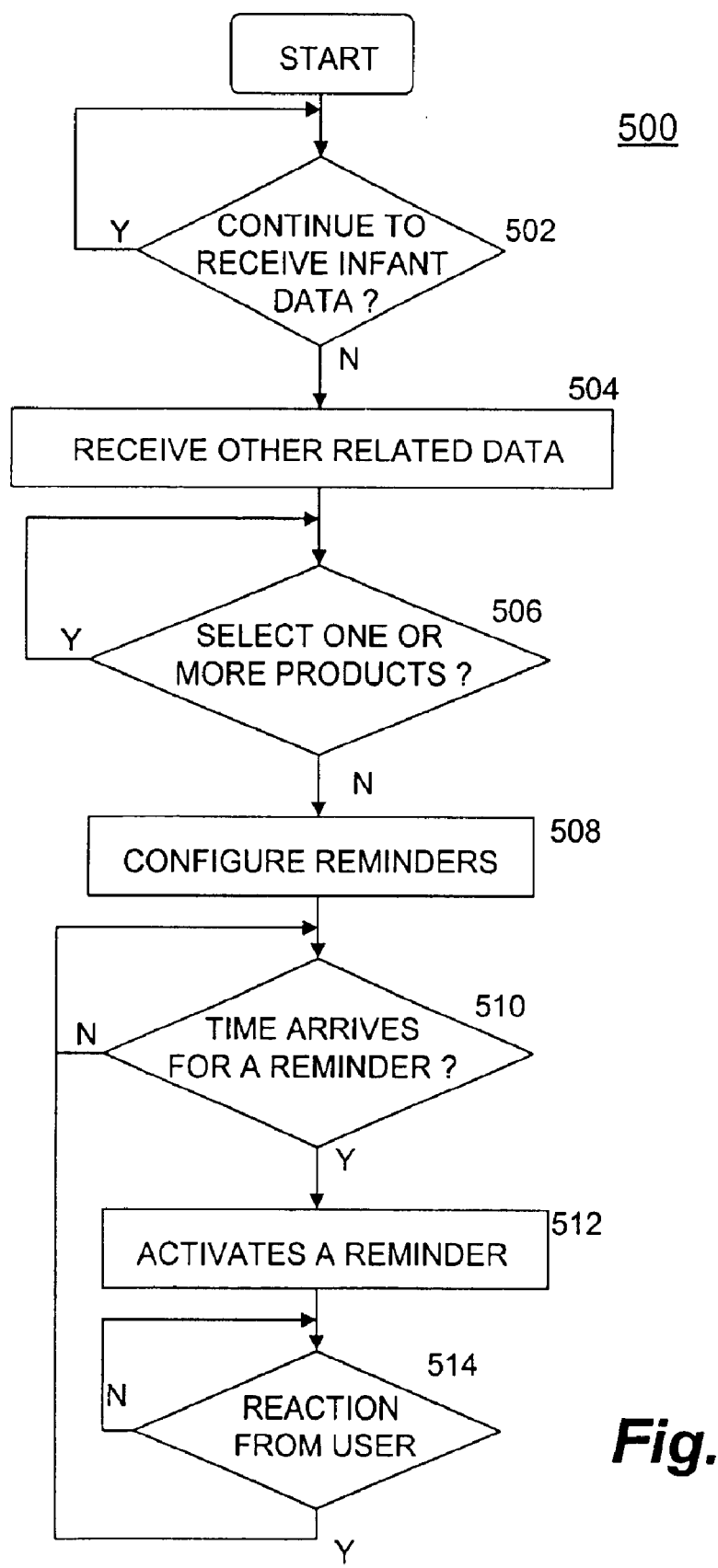
FIG. 5 is a flow diagram of a process associated with a portable device facilitating the care of an infant according to one embodiment of the present invention.

FIG. 5 is a flow diagram of the process 500 associated with a portable device facilitating the care of an infant according to one embodiment of the present invention. The process 500 may be implemented in a software module or in hardware, or a combination of both. At 502, the process 500 continues to receive infant data from the user till all required data is received. Typically the required infant data may include a name, weight, birth date, gender of the infant. At 504, the process 500 may be configured to receive additional data about the infant. The additional data may include health conditions of the infant, for example, the weight is a little off the normal and the infant cries more than usual. After the additional data is received, the process 500 moves to 506 to receive a selection of a list of infant products provided. In general, the process 500 is configured to support a number of different types or brands of infant products, each may have different level of density, nitration, and use. The selection of certain products will ensure the accuracy of configuring reminders at 508.

Given the entered infant data and information on the selected products to use for the infant, at 508, the reminders are configured in accordance with some recommended care data for a health child. For example, an infant of 8 pounds is recommended to be fed 2 oz of AAA formula every 2 hours in the first two weeks, the amount is gradually increased to 2.2 oz for the next week and continued to increase proportionally as the infant grows. According to the recommended care data, the reminders are readily determined at 508.

Now the process 500 enters the waiting mode in synchrony with the time at 510 pending the reminders to go off sequentially at 512. For example one reminder is automatically determined to go off at 11:30 AM, when the time is 11:30 AM, the reminder is automatically launched. At 514, the process awaits an interaction form the user. Typically, the reminder is configured to trigger a beeper or ringer in the portable device that can alarm the user. The reaction from the user may include an activation of a designated button that may bring up the reminder on a display or detailed instruction contained in the reminder.

Figure 6:
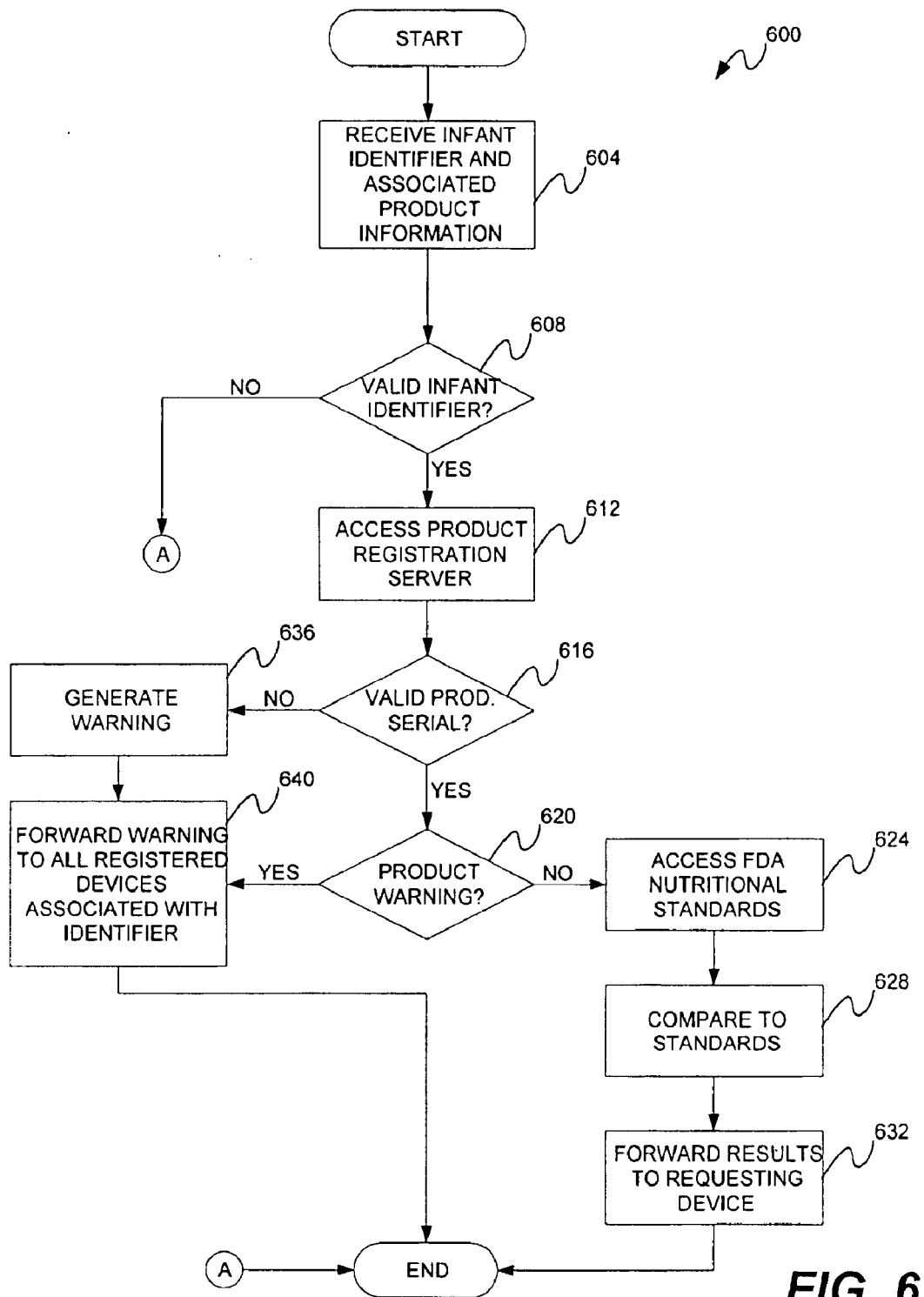
FIG. 6 is a flow diagram of the process associated with product validation and nutritional analysis system in accordance with a preferred embodiment of the present invention.

FIG. 6 is a flow diagram of the process 600 associated with product validation and nutritional analysis system in accordance with an embodiment of the present invention and may be used in conjunction with the server 104 or 114 in FIG. 1B. Optionally, the process 600 can be used to support or enhance the process 500 in FIG. 5. Depending on an exact implementation of the present invention, the process 600 may be implemented in software, hardware or a combination of both.

After a terminal device used by a user is connected to a server that is providing product or nutrition data, typically a request message is transmitted from the device to the server. The message may include the user's ID or the infant identifier or the device ID so that the server knows where the message comes from. Generally, the user needs to update the product information to ensure that the infant receives timely updated instructions. At 604 infant identification information and associated product information is received (i.e., product serial number). If the infant identifier is invalid then the process is concluded and an appropriate error message is forwarded to a requesting terminal device. If the infant identifier is valid then the server is permitted to access at 612 and a determination is made as to whether the provided product information matches entries received from a trusted third party at 616. If the product information matches entries received from a trusted third party then a determination is made at 620 as to whether there are any notices (i.e., product recalls or warnings) associated with the subject product information. If there are no associated notices then a standards database is accessed at 624 (i.e., FDA nutritional standards), the nutritional content of the subject product is compared to the given standards at 628 and a report is generated and forwarded to the designated terminal device at 632 as required. If the given product information is not registered or is the subject of a notice then the appropriate warning message is forwarded to the designated terminal devices.

The many features and advantages of the present invention are apparent from the written description, and thus, it is intended by the appended claims to cover all such features and advantages of the invention. Further, since numerous modifications and changes will readily occur to those skilled in the art, it is not desired to limit the invention to the exact construction and operation as illustrated and described. Hence, all suitable modifications and equivalents may be considered to fall within the scope of the invention.

I claim:

1. An apparatus for managing infant care, the apparatus comprising:
   a user interface including a display screen and an input mechanism;
   a memory device for storing infant data entered through the input mechanism;
   a memory space storing a set of reference data;
   a module determining reminders with respect to the entered infant data, each of the reminders to be activated by the module when an appropriate time comes; and
   wherein each of the reminders causes a message to be displayed on the display screen and the message instructs what to do with an infant under care, and the module collects the message in each of the reminders that has been activated and performs a comparison between the reference data and a set of actual data derived from the collected message, and wherein the comparison can be displayed, if needed, on the display screen so that the user knows how the infant is physically developing comparing to other normal children.

2. The apparatus of claim 1, wherein the infant data includes personal information particular to the infant under care of a user associated with the apparatus and the infant data is provided by the user.

3. The apparatus of claim 2, wherein the personal information includes birth date, birth weight, gender of the infant.

4. The apparatus of claim 3, wherein the personal information further includes health condition of the infant.

5. The apparatus of claim 2 further comprising an alerting means operatively connected to the processor and the client module, the alerting means alarming the user when one of the reminders is activated.

6. The apparatus of claim 5, wherein the alerting means is one or more of (i) a beeper, (ii) a vibrator, (iii) an unusual display, and (iv) a ringer.

7. The apparatus of claim 1, wherein the entered infant data in the memory device can be updated with newly entered infant data, as a result, the reminders are re-configured with respect to the newly entered infant data.

8. The apparatus of claim 1, wherein the apparatus is portable and carried around by a user.

9. The apparatus of claim 8, wherein the apparatus possesses a toy-like appearance suitable for an infant room.

10. The apparatus of claim 1, wherein the comparison is presented in a format that is one of (i) a graph, (ii) a table, and (iii) a text.

11. An apparatus for managing infant care, the apparatus comprising:
    a user interface including a display screen and an input mechanism;
    a memory device for storing a set of reference data and infant data entered through the input mechanism;
    a module receiving respective reminders entered by a user through the input mechanism, each of the reminders configured, when activated, to display a message reminding the user what to do, wherein the module collects the message in each of the reminders that has been activated, and performs a comparison between the reference data and a set of actual data derived from the collected message, and wherein the comparison can be displayed, if needed, on the display screen so that the user knows how the infant is physically developing comparing to other normal children, and
    wherein the apparatus is portable and possesses a toy-like appearance suitable for an infant room.

12. The apparatus of claim 11, wherein the infant data includes personal information particular to the infant under care of the user and the infant data is provided by the user.

13. The apparatus of claim 12, wherein the personal information includes birth date, birth weight, gender of the infant.

14. The apparatus of claim 11 further comprising an alerting means operatively connected to the processor and the client module, the alerting means alarming the user when one of the reminders is activated.

15. The apparatus of claim 14, wherein the alerting means is one or more of (i) a beeper, (ii) a vibrator, (iii) an unusual display, and (iv) a ringer.

16. An apparatus for managing infant care, the apparatus comprising:
    a user interface including a display screen and an input mechanism;

a memory device for a set of reference data and storing infant data entered through the input mechanism;

a module determining reminders with respect to the entered infant data, each of the reminders to be activated by the module when an appropriate time comes; the module collects the message in each of the reminders that has been activated and performs a comparison between the reference data and a set of actual data derived from the collected message, and wherein the comparison can be displayed, if needed, on the display screen so that the user knows how the infant is physically developing comparing to other normal children, and wherein each of the reminders causes a message to be displayed on the display screen and the message instructs what to do with an infant under care.

17. The apparatus of claim 16 further comprising a network interface that facilitate data communication with a server device over a data network, wherein the server device hosts a knowledge data base including product information of the infant product.

18. The apparatus of claim 17, wherein the apparatus is caused to download product information into the memory device when desired.

19. The apparatus of claim 17, wherein the product information includes nutritional information as well as usage instructions of the infant product.

20. The apparatus of claim 17, wherein the product information is provided by a manufacturer of the infant product or a business entity associated with the infant product.

21. An apparatus for managing infant care, the apparatus comprising:

a telephonic means for voice communication with other phones;

a memory device for storing a set of reference data and infant data entered through a keypad;

a client module, when activated by a processor, determining reminders according to at least an infant product with respect to the entered infant data, each of the reminders to be activated by the client module when an appropriate time comes, wherein the client module collects the message in each of the reminders that has been activated and performs a comparison between the reference data and a set of actual data derived from the collected message, and wherein the comparison can be displayed, if needed, on the display screen so that the user knows how the infant is physically developing comparing to other normal children, each of the reminders causes a message to be displayed on a display screen and the apparatus normally functions as a mobile telephone and becomes a reminding system when one of the reminders activates.

22. The apparatus of claim 21, wherein the entered infant data in the memory device can be updated with newly entered infant data, as a result, the reminders are re-determined with respect to the newly entered infant data.

23. A method for managing infant care, the method comprising:

entering infant data into a portable device;

selecting one or more desired products for an infant to be cared with the portable device;

receiving one of reminders that are configured in accordance with a set of reference data including the infant data and product information of the one or more desired products, wherein the reference data is updated with each of the reminders that has been activated; and following instructions included in the one of reminders when the one of reminders is displayed on a display screen of the portable devices;

updating the product information with a server providing latest information of the one or more desired products so that the reminders are always accurate.

24. A method for managing infant care, the method comprising:

receiving infant data from a caregiver caring an infant;

receiving a selection of one or more products for the infant;

configuring reminders in accordance with the infant data and product information of the selected one or more products, wherein the configuring of the reminders includes determining each of the reminders in accordance with a set of reference data that is also updated with each of the reminders that has been activated;

activating the reminders sequentially over time to remind the caregiver of what, when, and how much of the selected one or more products the infant shall be fed;

updating the product information with a server providing latest information of the one or more desired products so that the reminders are always accurate.

25. The method of claim 24 further comprising:

communicating over a network with a server;

receiving newly released product information of the selected one or more products, if there is any, to update the product information of the selected one or more products;

receiving regulated information of the selected one or more products, if there is any, to warn the caregiver that the selected one or more products are in question.

26. The method of claim 24 wherein each of the one or more products can be independently provided to the infant and have different levels of nutrition and favors.

27. The method of claim 24, wherein the activating of the reminders sequentially over time comprises displaying one of the reminders at a time and alerting the caregiver of the one of the reminders being displayed.

28. The method of claim 24, wherein the server is operated by a business producing the one or more products or administrating the product information of the one or more products.

* * * * *